United States Patent [19]

Molina

[11] 4,069,419
[45] Jan. 17, 1978

[54] DRY DEVELOPER COMPOSITION FOR DYE PENETRANT INSPECTION AND METHOD FOR EMPLOYING SAME

[75] Inventor: Orlando G. Molina, Westminster, Calif.

[73] Assignee: Rockwell International Corporation, El Segundo, Calif.

[21] Appl. No.: 611,292

[22] Filed: Sept. 8, 1975

[51] Int. Cl.² ............................................. G03K 3/00
[52] U.S. Cl. ............................ 250/302; 252/DIG. 10
[58] Field of Search ..................... 252/408, DIG. 10; 250/302

[56] References Cited

U.S. PATENT DOCUMENTS

| | | | |
|---|---|---|---|
| 2,806,959 | 9/1957 | DeForest et al. | 250/302 |
| 2,848,421 | 8/1958 | DeForest | 252/408 |
| 3,083,297 | 3/1963 | Lockwood | 252/408 |
| 3,108,187 | 10/1963 | Thornbury | 250/302 |
| 3,349,041 | 10/1967 | Alburger | 252/301.19 |
| 3,429,826 | 2/1969 | Alburger | 252/301.19 |
| 3,456,110 | 7/1969 | Diperstein | 250/302 |
| 3,543,570 | 12/1970 | Mlot-Fijalkowski | 250/302 |
| 3,558,882 | 1/1971 | Mlot-Fijalkowski | 250/302 |
| 3,716,492 | 2/1973 | Graham et al. | 250/302 |
| 3,838,160 | 9/1974 | Molina | 250/302 |
| 3,915,885 | 10/1975 | Molina | 250/302 |

*Primary Examiner*—Harold A. Dixon
*Attorney, Agent, or Firm*—Charles T. Silberberg; Lee L. Humphries

[57] ABSTRACT

Dry developer composition in powder form for use in penetrant inspection of surface flaws in bodies, consisting essentially of silica, preferably fumed silica, e.g. the material marketed as Cab-O-Sil M-5, and talc, particularly the powder marketed as Desertalc Mikro 507, in certain relative proportions. The resulting powder developer is particularly effective when employed in a dye penetrant inspection process comprising applying to a part surface a fluorescent penetrant, and especially a dye penetrant containing as carrier for the dye a biodegradable surfactant comprised of certain aliphatic oxyalkylated alcohols, followed by application of such dry developer to the part surface to provide bright fluorescent indications of surface flaws when inspected under fluorescent illumination.

18 Claims, No Drawings

DRY DEVELOPER COMPOSITION FOR DYE PENETRANT INSPECTION AND METHOD FOR EMPLOYING SAME

BACKGROUND OF THE INVENTION

This invention relates to procedure and compositions for non-destructive testing of bodies composed for example of metal, ceramic or plastic, or detect defects and metallurgical conditions in the surface of such bodies, and is particularly concerned with certain dry developer compositions for non-destructive dye penetrant inspection of parts, particularly employed in conjunction with certain dye penetrants, the powder developers of the invention being particularly effective in providing bright, e.g. fluorescent, indications, and having additional important advantages and superior results in comparison with presently known and commerically available powder developers.

In known penetrant inspection methods for rapid location and evaluation of surface flaws, defects or cracks in test bodies or parts, a penetrant composition containing a fluorescent dye and which will penetrate the openings of the surface cracks or flaws in the part, is applied to the surface of the test body, and the excess penetrant composition is removed from the surface of the body. A developer composition is then applied to the part surface. Such developer can be in the form of a light colored powder, which contrasts with the color of the dye and which acts as a wick and causes the liquid penetrant containing the fluorescent dye which was retained in the cracks or surface flaws, to be drawn up out of the surface defects by capillary action, and to "bleed" through the developer. Excess developer is removed and the part is then exposed to invisible fluorescigenous light, and the location of the surface flaws is revealed by the emission of visible fluorescent light by the penetrant dye which was retained in the cracks or flaws after the penetrant composition was removed from the surface of the part.

In order to increase the sensitivity of fluorescent penetrant inspection methods, it has been sought to increase the brightness of fluorescence of the fluorescent penetrant dye and to increase the contrast between the light received from the fluorescent penetrant indicator and from adjacent areas of the test part, thereby obtaining increased sensitivity.

Various developer compositions for penetrant inspection of surface cracks and flaws have heretofore been employed. Thus, for example, U.S. Pat. No. 2,806,959 discloses finely powdered silica, preferably admixed with talc in a proportion of 80% silica and 20% talc; U.S. Pat. No. 2,848,421 discloses a composition comprising silica aerogel and talc; and my U.S. Pat. No. 3,803,051 discloses an improved developer composition consisting essentially of alumina, titanium dioxide, talc and silica, the latter employed in relatively small amounts ranging from about 2 to 25%, e.g. about 4 or 5% by weight.

However, most of the dry developer compositions of the prior art have the disadvantage that when excess dry developer is removed from a part surface by air blasting, a common method of removing excess developer prior to inspection of the developer treated surface, a substantial amount of the developer in the cracks adjacent the part surface, and containing liquid penetrant drawn into the developer from such cracks, is also removed, and hence in effect reducing the sensitivity and brightness of fluorescence of the fluorescent dye in the cracks and defects.

Further, many of the prior art developer compositions tend to agglomerate and cake and hence this reduces their sensitivity to penetrant inspection of very small cracks or microcracks in the surface being tested.

Further, certain of the prior art developer compositions are not compatible with certain metals such as titanium and high nickel alloys which are used particularly in the aerospace industry, because such compositions contain elements or components such as chlorine and sulfur, so that the resulting composition has a low pH when contacted by the liquid penetrant.

Also, some of the prior art compositions are toxic and hence present hazards in handling.

In my copending applications Ser. Nos. 444,432 now U.S. Pat. 3890007 and 444,433, now abandoned both filed Feb. 21, 1974, now Patent Nos. 3,915,885 and 3,915,886, respectively, there is disclosed novel dye penetrants which have improved washability and sensitivity characteristics, and which are biodegradable, containing as the vehicle for the dye, certain biodegradable nonionic oxyalkylated alcohols.

It is accordingly an object of the present invention to provide a simple dry developer composition particularly useful for fluorescent dye penetrant inspection of the surface cracks and defects of bodies, comprising a minimum of components, and which provides high sensitivity, bright fluorescence and sharp contrast between the light emitted from the fluorescent penetrant indicating the location and nature of cracks and imperfections in the body, and the adjacent areas of the part, particularly when employed in a dye penetrant inspection process in conjunction with a dye penetrant containing as vehicle for the dye certain biodegradable nonionic oxyalkylated alcohols, as disclosed in my above copending applications. Another object is the provision of a dry developer for dye penetrant inspection as described above, and having other important advantages including light free-flowing characteristics, compatibility with structural materials such as metals and alloys thereof, and which are essentially nontoxic and relatively inexpensive.

DESCRIPTION OF THE INVENTION

It has been found unexpectedly that bright fluorescent indications of high sensitivity are achieved in a dye penetrant inspection process employing the improved dye penetrants of my above copending applications, utilizing as carrier for the dye certain biodegradable nonionic oxyalkylated alcohols, as described more fully below, by application of a developer composition consisting essentially of silica and talc, following removal of excess dye penetrant. The respective components of the developer composition preferably are in powder form, the particles of such respective components being of small size, and having other physical characteristics noted below, and preferably such components are employed in certain proportions, as pointed out in detail hereinafter.

The dry powder developer formulation of the invention also has the unique characteristics and advantages of being unusually non-fluorescent under black light (fluorescent) illumination, causing the fluorescent penetrant to fluoresce brightly in relation and in contrast to the surrounding white powder developer, and such developer composition is unusually light, fluffy and free flowing and intimately contacts and is retained in the openings of the minute cracks or microcracks, as well as large cracks, in the surface of the body. Further, the developer composition of the invention is essentially neutral, having a pH of the order of about 7, and accordingly is highly compatible with all metals and metal alloys. Moreover, the dry powder developer composition hereof is essentially nontoxic and is accordingly readily handleable by personnel, and is economical.

It has been found that due to the substantially larger amount of silica employed in the invention composition as noted hereinafter, in comparison for example, to the relatively small amount of silica present in the four component composition of my above U.S. Pat. No. 3,803,051, and preferably of the order of about 4% by weight of silica, the presence of the substantially larger amount of silica in the invention composition, e.g. of the order of about 50%, by weight, produces a "gellifying" effect upon the microscopic exuded entrapments of dye penetrant in the cracks and defects of a part surface. Such "gellifying" effect or tendency toward gel formation when the dye penetrant in the cracks and flaws is drawn into the developer powder at the mouths of the cracks and flaws, as result of the silica in the developer acting on the nonionic oxyalkylated alcohol surfactant of the dye penetrant, is highly beneficial. Thus, the gellified exuded dye indications of entrapments of the penetrant in the cracks and flaws, resists disruption or removal from adjacent the mouth of the cracks and flaws by air blasting, the common method of removing excess developer prior to inspection of the part surface under suitable e.g. fluorescent or "black", light.

Various tests were carried out using the developer composition of the present invention in side by side comparison with the four component developer composition of my above U.S. Pat. No. 3,803,051, each such developer employed in conjunction with a dye penetrant of the types of my above copending applications utilizing the nonionic oxyalkylated alcohol surfactant thereof. The results showed that when utilizing the two component developer of the present invention, equal or greater sensitivity can be achieved therewith, as compared to the results achieved with the four component developer composition of my above patent. Thus, it has been found that a simple developer composition consisting of only two components, which are readily available, provides not only highly beneficial results according to the invention, but is highly economical.

The talc component of the developer composition functions particularly as fluorescent penetrant brightener. This component is a fine white powder of small but irregular particle size. A commercially available material particularly suitable for purposes of the invention is that marketed as Desertalc Mikro 507, by Desert Minerals, Inc. of Los Angeles, California. The latter material is a semi-tremolitic-acicularplatey having a particle size distribution ranging from about 15 to less than 1 micron, and is essentially a calcium-magnesium silicate. This white powder provides a unique combination of highly irregular particle sizes and shapes, leaving an almost invisible film deposit of microsize particles which provide a path for entrapment of fluorescent penetrant which exudes from cracks and microcracks in the surface to which the developer is applied. Such fine powdery talc adheres to almost any type of surface including very fine or polished surfaces such as polished chrome plating. Due to the irregular particle size content of such talc, it functions as an aid to depositing the developer in varying size cracks.

Other suitable talcs include Desertalc Mikro 706, 707 and 906. Desertalc Mikro 706 and 707 are ultra-fine micaceous particle structures of thin, soft translucent plates. Desertalc Mikro 906 is a steatic-platey, spherical material having a structure of fine small platelets and sphere of high uniformity. This material is low in carbonate and is non-abrasive. Particle sizes of Desertalc 706, 707 and 906 are similar to 507, ranging from 15 to less than 1 micron.

The above described talcs, illustrated by Desertalc Mikro 507, 706, 707 and 906 have a different structure from conventional talc.

The second essential component of the invention composition is silica, employed also preferably in fine powder form of particle size ranging from about 0.007 to about 0.050 micron (about 70 to about 500 Angstroms), and is an extremely fluffy, snow-white powder of extremely low bulk density. A commercially available form of this component is marketed as Cab-O-Sil M-5 by Cabot Corporation. The Cab-O-Sil has an enormous external area, one gram of Cab-O-Sil M-5 having about 400 square meters of surface area. Cab-O-Sil M-5 is a submicroscopic fire-dry fumed silica different in structure from precipitated silicas or silica gels or aerogels. This white silica powder imparts free-flowing, non-caking properties to the overall powder developer composition, and also aids in developing bright fluorescent indications of fluorescent penetrants.

It has been found that in order to obtain effective results with the developer composition of the invention, the components thereof should be employed in certain proportions. Thus, the talc component is generally employed in an amount ranging from about 25 to about 65%, preferably from about 40 to about 60%, and the silica component generally in an amount ranging from about 35 to about 75%, preferably from about 40 to about 60%, by weight of the composition. It is accordingly seen particularly that the silica is employed in substantial or major proportions, an optimum composition producing outstanding results consisting of about 50% talc, especially Desertalc Mikro 507, and about 50% silica, especially Cab-O-Sil M-5, by weight.

As previously pointed out, the substantial proportion of silica in the developer composition and present in the openings of the cracks and discontinuities of a part after removal of excess developer from the part surface, combines with the dye penetrant, and more specifically with the oxyalkylated alcohol surfactant vehicle of the dye penetrant employed, to change such liquid vehicle to gel, such gel thus holding the dye penetrant, including the liquid vehicle of the penetrant and the dye therein, drawn out of the crack openings, at its location at the crack openings, and preventing the dye penetrant and developer adjacent the crack openings from being blown out of the cracks when excess developer is removed from the part surface by air blasting. It was unexpected to find that an extremely thin film of dye penetrant containing the above oxyalkylated alcohol surfactant can be converted to a gel when contacted with a developer according to the invention, having a high content of silica, without further mechanical action or agitation. This phenomenon occurs at a microscopic level because of the very small amounts of penetrant present at the openings of cracks on a part to be inspected, but the "build up" of the penetrant indications at the cracks and flaws, and the adherence of the penetrant to the part surface at the crack indications results from the "gellifying" effect of the silica present in high proportions in the developer. The end result is bright indications of high sensitivity when the part is viewed under suitable, e.g. fluorescent, light.

On the other hand, the gel forming effect is not obtained when employing the four component developer of my above patent because of the substantially reduced content of silica in such developer.

Illustrative examples of developer compositions according to the invention but not in limitation thereof, are set forth in Table I below, the amounts of the respective components being expressed in terms of percent by weight.

TABLE I

| COMPONENT | COMPOSITIONS (% by wt.) | | | | | | | |
|---|---|---|---|---|---|---|---|---|
| | A | B | C | D | E | F | G | H |
| Desertalc Mikro 507 | 50 | 40 | 45 | 55 | 60 | 65 | 70 | 75 |
| Cab-O-Sil M-5 | 50 | 60 | 55 | 45 | 40 | 45 | 30 | 25 |

As previously noted, compositions A is the optimum composition, providing a developer of high performance and very high sensitivity.

The high content silica developer of the present invention is particularly effective when employed in combination with the dye penetrant compositions of my above copending applications, wherein certain nonionic oxyalkylated alcohols are employed as carrier for the dye.

Thus, the nonionic biodegradable solvent or carrier employed essentially as the sole vehicle or carrier for the dye of such dye penetrant composition utilized in the invention process in conjunction with the developer of the invention, can be alkylene oxide condensation products prepared by the reaction of an organic compound having a reactive hydrogen atom, such as an aliphatic alcohol, with ethylene oxide, propylene oxide, or mixtures thereof. More particularly, one class of such nonionic solvents or carriers can be defined as straight chain, primary, aliphatic oxyalkylated alcohols, generally in the form of mixtures thereof, wherein the primary aliphatic alcohols can have from 8 to 20 carbon atoms, preferably 10 to 18 carbon atoms, and the oxyalkyl groups are ethylene oxide and propylene oxide, preferably in the form of a mixture thereof.

One class of nonionic carriers within the broad class of materials defined above is a cogeneric mixture of compounds represented by the formula:

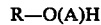

wherein:

R is an essentially linear alkyl group having from 10 to 18 carbon atoms, with the proviso that at least 70 weight percent of said compounds in said mixture have an R of from 12 to 16 carbon atoms, and A is a mixture of oxypropylene and oxyethylene groups, said oxypropylene and oxyethylene groups being from 55% to 80% of the total weight of the compounds, the oxypropylene to oxyethylene ratio of said total weight being from 0.85:1 to 2.75:1, preferably 1.25:1 to 2.25:1.

Another preferred class of condensation products or oxyalkylated alcohols within the above definition are those wherein the aliphatic alcohols of the oxyalkylated alcohols, or R in the above formula, ranges from 12 to 18 carbon atoms, and the total number of ethylene oxide and propylene oxide groups in the mixture thereof, or designated A in the above formula, ranges from about 4 to about 14.

The term "cogeneric mixture" as employed herein, designates a series of closely related homologues obtained by condensing a plurality of oxide units, with an alcohol or a mixture thereof. As is known, when a mixture of this type is generated, various oxyalkylene chain lengths are obtained.

Alcohols which may be employed in the preparation of the products noted above are those essentially linear, primary, aliphatic alcohols having from 8 to 20 carbon atoms, preferably 10 to 18 carbon atoms. Mixtures of alcohols are usually preferred since their use provides for a good balance of properties in the resulting products. Examples of alcohols which are operable include decyl alcohol, undecyl alcohol, lauryl alcohol, tridecyl alcohol, tetra-decyl alcohol, pentadecyl alcohol, cetyl alcohol, heptadecyl alcohol, stearyl alcohol, hydrogenated tallow alcohol, and mixtures thereof. They may be naturally-derived such as from coconut oil or synthetically-derived such as from linear alkanes or linear olefins.

The above nonionic biodegradable surfactants employed as carrier or vehicle for the dye of the penetrant solution employed according to the invention, are prepared by condensing an alcohol or mixture of alcohols, as described above, with a mixture of ethylene oxide and propylene oxide, in the presence of an alkaline catalyst, such as potassium hydroxide. The oxide mixture may be added to the alcohol in one continuous step or it may be added in several steps. The products thus produced possess random distribution of oxyethylene and oxypropylene groups.

The nonionic surface active agents described above and their method of preparation are disclosed in U.S. Pat. No. 3,504,041, and such disclosure is incorporated herein by reference. These surface active agents are believed to include, for example, that class of surfactants which are marketed as the "Plurafac" surfactants "RA-40" grades.

Another class of biodegradable liquid, water miscible oxyalkylated alcohol condensation products within the above definition are those wherein the aliphatic alcohol, or R, is a straight chain alkyl group having from 8 to 20 carbon atoms, the number of ethylene oxide groups in the mixture thereof with propylene oxide, or A, ranges from 3.75 to 12.75, and the number of propylene oxide groups in such mixture ranges from 1.7 to 7.0, the oxyethylene to oxypropylene ratio in such mixtures being from 1.8:1 to 2.2:1. Such cogeneric mixtures can be prepared in two steps, the first step being condensation of an alcohol mixture and ethylene oxide in the presence of an alkaline condensing agent or catalyst, to form an ethoxylated product, followed by condensing the resulting ethoxylated product with propylene oxide. There can be employed in such reaction a mixture of straight chain aliphatic alcohols having from 8 to 20 carbon atoms in the aliphatic chain. This cogeneric mixture of condensation products and the method of their preparation are disclosed in U.S. Pat. No. 3,340,309, and such disclosure is also incorporated herein by reference. The nonionic oxyalkylated alcohols marketed as the "RA-20" grades of "Plurafac", are believed representative of the class of surface active agents disclosed in the latter patent.

Various other "Plurafac" grades which are marketed and are believed to be generally within the above-described classes of oxyalkylated alcohol surfactants are those designated RA-43, A-24, A-25, B-25-5, and B-26 and D-25.

A class of particularly preferred nonionic biodegradable solvents or carriers which can be employed as substantially the sole vehicle for the dye of the dye penetrant compositions in the present invention process are ethoxylates of a mixture of linear secondary aliphatic alcohols, with the hydroxyl groups randomly distributed, the linear aliphatic hydrophobic portion of such alcohols being a mixture of alkyl chains containing in the range from 10 to 17 carbon atoms, preferably from 11 to 15 carbon atoms, and containing an average of from 3 to 12 moles of ethylene oxide.

The above particularly preferred class of nonionic biodegradable surfactant employed as carrier for the dye penetrant of the invention is a mixture of compounds which can be represented by the formula:

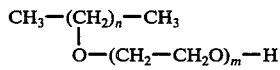

wherein $n$ is in the range from 9 to 13, and $m$ is an average of 3 to 12.

Although preferably each of the immediately abovedefined surfactants is formed of a mixture of two or more linear alkyl hydrophobic chains ranging from $C_{11}$ to $C_{15}$ as noted below, the surfactant can contain a single such chain formed from a single secondary aliphatic alcohol of the types described below.

The linear alkyl hydrophobic portion of the above defined surfactant is a mixture of $C_{11}$ to $C_{15}$ linear alkyl chains, and can be derived from a mixture of $C_{11}$ to $C_{15}$ aliphatic secondary alcohols, for example the secondary undecyl, dodecyl, tridecyl, tetradecyl and pentadecyl alcohols. The hydrophilic portion of the surfactant is a polyoxyethylene chain randomly attached to any carbon atom of the linear alkyl hydrophobic chains, other than to the terminal carbon atoms thereof, through an ether linkage. It will accordingly be understood that the specific carbon atom or —$CH_2$— group in the alkyl hydrophobic chains to which the hydrophilic polyoxyethylene chain is attached will become a

group in the above structural formula. Such hydrophilic polyoxyethylene chain is generally expressed in terms of an average number of moles of ethylene oxide.

Illustrative examples of biodegradable nonionic surfactants of the types defined in the above formula are those consisting of a mixture of ethoxylates of from 11 to 15 carbon atoms in the aliphatic hydrophobic chain, and which have an average of 3, 5, 7, 9 and 12 moles of ethylene oxide, respectively, as the hydrophil.

Materials corresponding to these five examples of biodegradable nonionic surfactants are marketed, respectively as:

| Tergitol | 15-S-3 |
| " | 15-S-5 |
| " | 15-S-7 |
| " | 15-S-9 |
| " | 15-S-12 |

In each case of the Tergitol S series of surfactants listed above, the number to the left of the "S" indicates a hydrophobic aliphatic chain of from 11 to 15 carbon atoms derived from a mixture of alcohols on $C_{11}$ to $C_{15}$ backbone chains, and the number to the right of the "S" designates the average number of moles of ethylene oxide as the hydrophil. Thus for example, Tergitol 15-S-5 is a mixture of linear aliphatic alcohols in the $C_{11}$ to $C_{15}$ range ethoxylated with an average of 5 moles of ethylene oxide. All of these commercially marketed Tergitol S series of surfactants are water soluble except for Tergitol 15-S-3, which is essentially water insoluble. Mixtures of these materials can also be employed in providing the dye penetrant utilized according to the invention, such as a mixture of the above Tergitols 15-S-5 and 15-S-3; a mixture of 15-S-3 and 15-S-9; and a mixture of 15-S-5 and 15-S-9.

The above preferred class of nonionic biodegradable surfactants employed as carrier or vehicle for the dye of the penetrant solution used in the invention process are prepared by reacting an alcohol or mixture of alcohols, as described above, with the desired proportion of ethylene oxide, in the presence of an alkaline catalyst, such as potassium hydroxide. The ethylene oxide may be added to the alcohol or mixture of alcohols in one continuous step or it may be added in several steps. The products thus produced process random distribution of oxyethylene groups, as noted above.

Another process for preparing the above preferred nonionic surfactants in the form of ethoxylates of linear secondary aliphatic alcohols, is described in U.S. Pat. No. 2,870,220.

Any suitable dye generally employed in dye penetrant compositions can be incorporated into the nonionic oxyalkylated alcohol surfactants described above for producing the dye penetrant compositions employed in the invention process. Preferably, however, a fluorescent dye is employed for this purpose. The oxyalkylated surfactant vehicle for the dye is compatible therewith and has the ability to dissolve either small or relatively large amounts of the dye and to hold a high concentration of dye in solution while providing good resolution and clarity of the dye trace in the cracks and flaws.

As previously noted, the dye penetrant solution employed according to the invention process preferably contains a fluorescent dye. Various types of fluorescent dyes can be employed including for example the dye marketed as Fluorol 7GA and Morton Fluorescent Yellow G, as well as other fluorescent dyes such as those marketed as Calcofluor Yellow, Azosol Brilliant Yellow 6GF; Rhodanine B, Rhodanine 6 GDN, Calcolfuor White RW, Blancophor White AW, Auramine and Eosine G, and water soluble fluorescent dyes such as Blancophor FFG.

The dye penetrant composition employed in the invention process alternatively can contain non-fluorescent or daylight type dyes such as azo types dyes, e.g., xylenaezobeta-naphthol, Mefford No. 322 dye, believed to be o-tolueneazoxyleneazo-beta-naphthol, and the azo dyes marketed as Oil Red "O" and Sudan Red. These dyes conveniently can be employed where daylight or white light is only available, particularly where the surface of the body to be detected contains relatively gross cracks. However, it is preferred to employ fluorescent dyes having greater sensitivity or detectability as result of the high contrast obtained by the fluorescent indications.

The amount of dye which is incorporated into the oxyalkylated alcohol surfactant or carrier to produce the dye penetrant composition of the invention, can range from about 0.1 to 15, preferably about 0.5 to about 10, parts of the dye, or mixtures thereof, per 100 parts of the oxyalkylated alcohol surfactant, by weight. In preparing the dye penetrant composition employed in the invention process, the dye is simply added to the oxyalkylated alcohol carrier, in the desired proportion. The resulting dye penetrant composition has both high and low temperature stability.

Although Tergitol 15-S-3 is essentially water insoluble and is usually employed in combination with the other members of the Tergitol S series noted above, such as Tergitol 15-S-5, dye penetrant compositions according to the invention containing Tergitol 15-S-3 alone, can be employed. However, Tergitol 15-S-3 has its greatest utility for production of dye penetrants having high sensitivity according to the invention, when employed in combination with the other water washable and water soluble Tergitols such as Tergitol 15-S-5 and Tergitol 15-S-9. Also, particularly effective dye penetrants are provided according to the invention employing a combination or mixture of the above Tegitols 15-S-5 and 15-S-9, and to which there can be added optionally Tergitol 15-S-3, as described in my copending application Ser. No. 521,730 filed Nov. 7, 1974, now U.S. Pat. No. 3,934,092.

Typical liquid dye penetrant compositions which can be employed in the invention process in conjunction with the dry developer of the invention are as follows:

TABLE II

| COMPONENTS | Liquid Compositions (Parts by Weight) | | | | | | | |
|---|---|---|---|---|---|---|---|---|
| | A' | B' | C' | D' | E' | F' | G' | H' |
| Tergitol 15-S-3 | — | — | — | — | 25 | — | — | — |
| Tergitol 15-S-5 | 100 | — | 75 | — | 75 | — | 75 | 75 |
| Tergitol 15-S-9 | — | — | 25 | — | — | 100 | 25 | 25 |
| Plurafac A-24 | — | 100 | — | — | — | — | — | — |
| Plurafac RA-43 | — | — | — | 100 | — | — | — | — |
| Calcofluor White RW | 5.0 | 5.0 | 5.0 | 5.0 | 2.5 | — | 2.5 | 1.25 |
| Fluorol 7 G A | 1.5 | 1.5 | 1.5 | 1.5 | 0.75 | — | 0.75 | 0.375 |
| Morton Fluorescent Yellow G | — | — | — | — | — | 2.5 | — | — |

The dye penetrant composition employed in the invention process, utilizing the above biodegradable nonionic oxyalkylated alcohol surfactants can be tailored to have varying degrees of sensitivity for detection of the smallest microcracks to gross cracks in a part surface by generally varying the amount of dye incorporated and also by selecting particular surfactants or combinations thereof.

In the method for detecting cracks and flaws in the surface of an object employing the above dye penetrant compositions and dry developer of the invention, such dye penetrant is applied to the part surface in any suitable manner, as for example, by spraying or brushing. After application of the dye penetrant to the surface of the test part, the excess dye penetrant composition is readily removed from the object surface by water washing, e.g. by application of a water spray or sprayed mixture of air and water. The dye penetrant compositions employed herein such as those containing the above noted Plurafaces and particularly those containing the above Tergitols 15-S-5 and 15-S-9, generally have excellent washability without removing dye penetrant from the cracks and defects on the part surface.

The developer composition of the invention is then applied to the part surface followed by removal of excess developer, as by means of an air blast, but leaving developer containing silica at the mouth of the cracks, the silica combining readily with the nonionic oxyalkylated alcohol surfactant as noted above to form thin films of gelled penetrant indications which remain after such air blasting. The part is then viewed under suitable lighting conditions, employing black light or fluorescent illumination when the dye penetrant containing a fluorescent dye.

Illustrative examples of practice of the invention are set forth below.

EXAMPLE 1

The fluorescent dye penetrant Composition A' of Table II above was applied as by spraying, to separate side-by-side halves of the surface of a chromium-plated brass test panel containing minute cracks of the order of 0.00002 to 0.0001 inch in width, closely distributed over its entire surface. A water wash was then applied as by an air-water spray over the coating of the dye penetrant Composition A' on each half surface of the test panel, causing instantaneous washing away of the dye penetrant on the half surfaces of the panel without dislodging the dye penetrant from the surface cracks and thus entrapping the penetrant therein.

One side of the test panel surface to which penetrant Composition A' above was initially applied, was then covered with the powder developer A of Table I above, and the other side of the test panel to which dye penetrant A' was applied was then covered with a prior art powder developer having the following composition, according to my above U.S. Pat. No. 3,803,051.

| COMPONENTS | Per cent by Weight |
|---|---|
| Talc | 52 |
| Alumina | 35 |
| Silica | 4 |
| TiO$_2$ | 9 |

In each case the above developers were permitted to dwell over the two half surfaces of the test panel for a period of about 2 minutes.

Excess developer composition in each case was then carefully removed from both half surfaces of the test panel by means of a gentle air blast.

The panel was then placed under black light (fluorescent) illumination and the respective half surfaces viewed in such illumination. It was observed that the first half side of the panel which had been treated with developer Composition A of the invention, disclosed fluorescent indications from numerous readily defined microcracks therein, such fluorescent indications being substantially brighter and revealing a greater concentration of the microcracks than the fluorescent indications from the microcracks on the half side of the panel which had been treated with the prior art developer, thus indicating increased sensitivity employing the developer of the invention in conjunction with a dye penetrant containing nonionic oxyalkylated alcohol as dye vehicle.

In the case of the first side of the test panel to which developer Composition A was applied, thin minute gel films appeared to form adjacent the crack openings, whereas in the case of the second side of the panel to which the prior art developer was applied, no such gel films appeared to form.

EXAMPLE 2

Dye penetrant inspection tests were carried out in a manner generally similar to the procedure of Example 1, employing a test panel containing cracks of intermediate size, and a test panel having gross cracks, and employing the dye penetrant Composition C' and the developer Composition E.

On each of the two test panels above, bright fluorescent indications were obtained from the cracks of intermediate size on one side of the first panel, and from the gross cracks on one side of the second panel, employing developer Composition E, comparable to the brightness and sensitivity of the fluorescent indications obtained employing developer composition A in Example 1, again indicating gel formation at the crack openings, of the dye penetrant in contact with the high silica content invention developer.

In the case of the opposite sides of both of the above test panels to which the prior art powder developer of Example 1 was applied, the sensitivity was reduced, no gel formation of the dye penetrant taking place in the presence of the prior art developer of reduced silica content.

EXAMPLE 3

The procedure of Example 1 was carried out except that the second side of the test panel was treated with the prior art dye penetrant composition of Example XI of my U.S. Pat. No. 3,838,160, containing N-methyl-2-pyrrolidone and isobutyl heptyl ketone as dye vehicle.

Here again fluorescent indications of higher sensitivity were obtained for the side of the panel treated with dye penetrant Composition A' containing oxyalkylated alcohol surfactant and developer composition A, as compared to the sensitivity of the indications from the other side of the test panel treated with the pyrrolidone-containing dye penetrant of my above patent and developer composition A.

This example shows that the developer composition of the present invention is particularly effective when employed in conjunction with the nonionic oxyalkylated alcohol surfactant of my above copending applications, due to the gel formation phenomenon discussed above, whereas the developer composition A does not convert the pyrrolidone type prior art dye penetrant of my above patent to a gel at the mouth of the cracks in the part.

EXAMPLE 4

Tests on aluminum panels having a very smooth surface and containing microcracks of the order of 0.00002 to 0.0001 inch in width, were carried out employing procedure similar to that employed in Example 1, utilizing dye penetrant Composition E' containing a combination of Tergitol 15-S-5 and Tergitol 15-S-3, and the developer Composition D.

Results obtained were similar to those obtained in Example 1.

EXAMPLE 5

The procedure of Example 1 was essentially followed, but employing in place of dye penetrant Composition A', a nonfluorescent water washable biodegradable dye penetrant solution according to the invention, consisting of 15 parts of Tergitol 15-S-5 and 1 part of Oil Red "O" dye, by volume.

Results of crack detectability were obtained similar to Example 1.

However, the brightness and sensitivity of the colored dye traces obtained employing the biodegradable non-fluorescent dye penetrant of this example were not as great as for the fluorescent biodegradable dye penetrant Composition A'.

The dry developer composition of the invention can be employed in conjunction with a dye, e.g. fluorescent, penetrant for penetrant inspection of cracks and microcracks as small as b 0.00002 inches, or less, wide in the surface of bodies of various materials, including, in addition to metals and alloys thereof, such as titanium, steel, copper and aluminum, ceramics, glass, plastics and rubber.

From the foregoing, it is seen that the invention provides a dry developer composition for fluorescent penetrant inspection of flaws in bodies, of improved properties and advantages over known and presently available commercial developers, particularly when employed in combination with a dye penetrant composition containing certain nonionic oxyalkylated alcohol surfactants as vehicle for the dye.

While I have described particular embodiments of my invention for the purpose of illustration within the spirit of the invention, it will be understood that the invention is not to be taken as limited except by the scope of the appended claims.

What is claimed is:

1. A method for detecting cracks and flaws in the surface of an object, which comprises applying to said surface a water washable biodegradable dye penetrant composition which consists essentially of (1) a biodegradable nonionic surfactant selected from the group consisting of (a) straight chain, primary, aliphatic oxyalkylated alcohols, wherein said alcohols can contain from 8 to 20 carbon atoms and the oxyalkyl groups are a mixture of ethylene oxide and propylene oxide groups, and (b) ethoxylates of linear secondary aliphatic alcohols, with the hyroxyl groups randomly distributed, the linear aliphatic portion of said alcohols being a mixture of alkyl chains containing in the range from 10 to 17 carbon atoms, and containing an average of from 3 to 12 moles of ethylene oxide and (2) a small amount of a dye soluble in said surfactant, removing said dye penetrant composition from said surface without removing liquid dye penetrant from said cracks and flaws in said surface, applying to said surface a dry developer composition consisting essentially of about 25 to about 65% talc and about 35 to about 75% of fumed silica, by weight, said fumed silica having a particle size less than the particle size of said talc, said dye penetrant composition in said cracks and flaws being converted to a gel when contacted with said developer composition, removing excess developer and viewing the surface of said object under lighting conditions to obtain colored traces from the dye in said cracks and flaws.

2. A method as defined in claim 1, said excess developer being removed by an air blast.

3. A method as defined in claim 1, wherein said talc is of fine particle size.

4. A method as defined in claim 3, said silica being present in an amount sufficient to convert said dye penetrant adjacent said cracks and flaws to a gel.

5. A method as defined in claim 3, said talc being present in an amount ranging from about 40 to about 60% and said silica being present in an amount ranging from about 40 to about 60%, by weight.

6. A method as defined in claim 3, said talc and said silica each being present in an amount of about 50% by weight.

7. A method as defined in claim 1, said dye being present in an amount ranging from about 0.1 to 15 parts, per 100 parts, by weight of said surfactant.

8. A method as defined in claim 1, wherein said dye is a fluorescent dye, and said surface of said object is viewed under fluorescigenous light to obtain colored fluorescent traces from the dye in said cracks and flaws.

9. A method as defined in claim 1, wherein said surfactant (a) is a mixture of compounds having the formula:

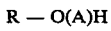

wherein R is an essentially linear alkyl group having from 10 to 18 carbon atoms, at least 70 weight percent of said compounds in said mixture having an R of from 12 to 16 carbon atoms, and A is a mixture of oxypropylene and oxyethylene groups, said oxypropylene and oxyethylene groups being from 55 to 80% of the total weight of said compounds, the oxypropylene to oxyethylene ratio of said total weight being from 0.85:1 to 2.75:1; and wherein said surfactant (b) is ethoxylates of a mixture of alcohols having the formula:

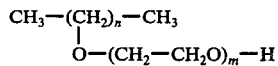

where $n$ is in the range from 9 to 13 and $m$ is an average of 3 to 12.

10. A method as defined in claim 9, wherein R in said surfactant (a) can have from 12 to 18 carbon atoms, and the total number of A groups can range from about 4 to about 14; and wherein in surfactant (b) the linear alkyl hydrophobic portion of said surfactant is a mixture of $C_{11}$ to $C_{15}$ linear chains, and the hydrophilic portion of said surfactant is a polyoxyethylene chain randomly attached to the linear alkyl hydrophobic chains through the ether linkage, and wherein said surfactant (b) is selected from the group consisting of said ethoxylates of said mixture of alcohols, wherein n ranges from 9 to 13, and m is an average of 3, 5, 7, 9 or 12.

11. A method as defined in claim 10, wherein said talc is of fine particle size, said talc being present in an amount ranging from about 40 to about 60% and said silica being present in an amount ranging from about 40 to about 60%, by weight.

12. A method as defined in claim 11, wherein said dye is a fluorescent dye, said excess developer being removed by an air blast, and said surface of said object is viewed under fluorescigenous light to obtain colored fluorescent traces from the dye in said cracks and flaws.

13. A method as defined in claim 1, said removing said dye penetrant composition from said surface being carried out by a water wash.

14. A method as defined in claim 12, said removing said dye penetrant composition from said surface being carried out by a water wash.

15. A method as defined in claim 10, wherein said surfactant is said surfactant (b).

16. A method as defined in claim 12, wherein said surfactant is said surfactant (b).

17. A method as defined in claim 15, wherein said surfactant (b) is a combination of said ethoxylates.

18. A method as defined in claim 16, wherein said surfactant (b) is a combination of said ethoxylates when $m$ is 5 and where $m$ is 9.

* * * * *